United States Patent [19]

Beutler et al.

[11] Patent Number: 4,677,059
[45] Date of Patent: Jun. 30, 1987

[54] PROCESS AND REAGENT FOR THE ENZYMATIC DETERMINATION OF SULPHITE

[75] Inventors: Hans-Otto Beutler, Tutzing; Ingrid Schütte, Eberfing; Walter Schneider, Weilheim, all of Fed. Rep. of Germany

[73] Assignee: Boehringer Mannheim GmbH, Mannheim-Waldhof, Fed. Rep. of Germany

[21] Appl. No.: 595,750

[22] Filed: Apr. 2, 1984

[30] Foreign Application Priority Data

Apr. 12, 1983 [DE] Fed. Rep. of Germany ....... 3313178

[51] Int. Cl.[4] .......................... C12Q 1/26; C12Q 1/28
[52] U.S. Cl. ...................................... 435/25; 435/28; 435/810
[58] Field of Search .................... 435/25, 28, 810; 436/904

[56] References Cited

U.S. PATENT DOCUMENTS 4,168,205 9/1979 Danninger et al. .............. 435/25 X

FOREIGN PATENT DOCUMENTS 2737290 3/1978 Fed. Rep. of Germany ........ 435/25
2806371 8/1979 Fed. Rep. of Germany ........ 435/25

OTHER PUBLICATIONS

*Enzyme Nomenclature*, (1973), Elsevier Scientific Publishing Company, pp. 96–97, 100–101.
Barmen, (ed) 1969, Enzyme Handbook, vol. I, p. 219.
Trends in Analytical Chemistry, Band 2, Nr. 1, Jan. 1983, Cambridge GB; N. T. Crosby "Enzymes in Food Analysis", Seiten VII, VIII.
M. Dixon, E. C. Webb, "Enzymes", 3. Auflage 3. Auflage 1979, Longman Group Ltd., London, GB, Seiten, 736–737.

*Primary Examiner*—Esther M. Kepplinger
*Attorney, Agent, or Firm*—Felfe & Lynch

[57] ABSTRACT

The present invention provides a process for the enzymatic determination of sulphite, wherein the sulphite is oxidized in a buffered solution with sulphite oxidase to give sulphate, the hydrogen peroxide thereby formed being reduced in the presence of NAD and NADH with the enzyme NADH peroxidase and the consumption of NADH being determined optically.

The present invention also provides a reagent for the enzymatic determination of sulphite, wherein it contains sulphite oxidase, NADH, NAD, NADH peroxidase and buffer.

23 Claims, No Drawings

PROCESS AND REAGENT FOR THE ENZYMATIC DETERMINATION OF SULPHITE

The present invention is concerned with a process and a reagent for the enzymatic determination of sulphite.

Sulphite is very frequently used in foodstuff technology because of its bactericidal and fungicidal properties and also because of its enzyme-inhibiting properties. In the case of fruit and vegetable products and of fruit juices, it is used as a preserving agent. Furthermore, sulphite inhibits the Maillard reaction and is, therefore, used in the production of potato products for the preventing of brown discoloration. In the production of wine, "sulphuring" is a measure which has been carried out by vintners for a very long time, the purpose of which is to prevent wine from becoming brown, to protect it against the development of pathogenic microorganisms and to remove acetaldehyde formed, in order to prevent the formation of acetic acid. Furthermore, as an inhibitor of many enzymes, sulphite also prevents undesired enzymatic reactions.

Therefore, although the technological importance of sulphite is very great, especially in the foodstuff field, the general use of this material is, however, limited because of its toxic properties. The health-damaging properties of sulphite require a precise control of the amount of sulphite in the foodstuffs in question. Because of the health-damaging properties, certain maximum amounts of sulphite in foodstuffs are legally laid down. From this follows the necessity of determining the sulphite concentration in many foodstuffs.

The previously known methods for determining sulphite, especially in foodstuffs, are very unsatisfactory. As a rapid test in foodstuff chemistry laboratories, there is used an iodometric determination which, however, not only determines sulphite but also all other reducing substances present. This method is very non-specific but requires a relatively small expenditure of time and is, therefore, preferred for routine investigations. A more specific official method used in the Federal Republic of Germany for determining the sulphite content of wine involves heating with phosphoric acid, the sulphurous acid liberated being distilled over into a receiver containing a hydrogen peroxide solution which oxidises the sulphurous acid to sulphate, whereafter the sulphate is determined. However, this method is very time-consuming.

Therefore, it is an object of the present invention to provide a process for the determination of sulphite which is not only specific for sulphite but can also be carried out in only a short time.

Thus, according to the present invention, there is provided a process for the enzymatic determination of sulphite, wherein the sulphite is oxidised to sulphate in a buffered solution with sulphite oxidase, the hydrogen peroxide thereby formed being reduced in the presence of NAD and NADH with the enzyme NADH peroxidase and the consumption of NADH being determined optically.

It is surprising that an enzymatic method could be found for the determination of sulphite since, on the one hand, it was to have been feared that the hydrogen peroxide formed by the redox reaction would immediately react with the reducing sulphite still present in the solution, which would falsify the results obtained and, on the other hand, a known property of sulphite is the inhibition of enzymes so that an enzymatic determination of the resultant hydrogen peroxide would not appear to be capable of being carried out. A detection of the resultant hydrogen peroxide in the usual manner by way of the formation of a coloured material in the presence of peroxidase also appeared to offer no prospects since the coloured material present in oxidised form will react with sulphite still present to give a leuco coloured material present in reduced form and peroxidase is inhibited by sulphite. However, with the help of the process according to the present invention, it is, surprisingly, now possible to provide an enzymatic method for the determination of sulphite with which sulphite can be determined specifically and quickly.

The process according to the present invention takes place in two steps. First, the sulphite present in buffered solution is oxidised with the help of the enzyme sulphite oxidase (SO$_2$-OD) (E.C. 1.8.3.1) in the presence of oxygen to give sulphate, according to the equation:

$$SO_3^- + O_2 + H_2O \xrightarrow{SO_2-OD} SO_4^- + H_2O_2 \quad (1)$$

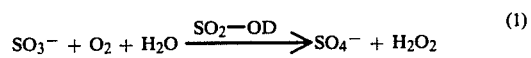

The hydrogen peroxide formed reacts immediately in the presence of NAD with NADH and NADH peroxidase (E.C. 1.11.1.1) with the formation of water according to the equation:

$$H_2O_2 + NADH + H^+ \xrightarrow{NADH-POD} 2H_2O + NAD^+ \quad (2)$$

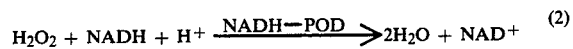

NADH thereby acts as a reducing agent and is oxidised to NAD$^+$. Since NADH and NAD$^+$ absorbed at different wavelengths, the decrease of NADH can be evaluated optically. The amount of NADH consumed by the reaction is equivalent to the amount of sulphite in the sample solution. NADH can be easily determined quantitatively on the basis of its absorption at, for example, 365, 340 or 334 nm.

The reaction is carried out in a buffered solution, the pH of which is in the range of from 7.5 to 8.5, the preferred pH range being from 7.8 to 8.2.

Various buffer substances can be used for the sulphite determination. Glycylglycine, imidazole, tris and triethanolamine buffers can, for example, be used, triethanolaline buffer being especially preferred. The concentration of the buffer does not have a great influence on the course of the test. A concentration of the buffer in the range of from 0.05 to 0.4 mol/liter has proved to be suitable, the range of from 0.1 to 0.3 mol/liter being especially preferred.

The amount of NADH necessary for the determination should not be too great in order that the extinction for the initial value remains in a readily measurable range but, on the other hand, it should not be too low in order that the reaction can still proceed quantitatively. A concentration of NADH in the range of from 100 to 500 μmol/liter has proved to be preferable, an amount of from 125 to 225 μmol/liter NADH being especially preferred.

Furthermore, NAD is added to the test solution, an amount of from 0.5 to 2.0 mMol/liter NAD having proved to be sufficient, although larger amounts can be used. The addition of 0.75 to 1.00 mMol/liter NAD is especially preferred.

The amount of NADH peroxidase is not critical. If, however, too little activity is used, then the reaction time becomes long and the sulphite content determined can sometimes be too low. Therefore, at least 10 U/liter NADH peroxidase should preferably be added to the sample solution. Amounts above 100 U/liter NADH peroxidase do not result in any further reduction of the reaction time and are, therefore, uneconomical. It has proved to be preferable to use a concentration of NADH peroxidase of 10 to 100 U/liter, an amount of from 40 to 80 U/liter being especially preferred.

The amount of the enzyme sulphite oxidase needed for the oxidation of the sulphite to sulphate is also not critical. However, an activity of less than 25 U/liter of sulphite oxidase has proved to be less preferable since the reaction time then becomes too long and the amount of sulphite determined decreases. Therefore, the sulphite oxidase is preferably used in an amount of from 25 to 75 U/liter. A higher activity of sulphite oxidase is possible but is uneconomic since it does not result in any further improvement. The sulphite oxidase is especially preferably used in the range of from 35 to 60 U/liter.

The process according to the present invention is specific for sulphite. However, comparatively large amounts of ascorbic acid in the sample material can disturb the test. Since sulphite must especially be detected in fruit and vegetable products and in fruit juices, which contain ascorbic acid in more or less large amounts, it has proved to be expedient to remove the ascorbic acid before the analysis. An appropriate process for the removal of ascorbic acid is the addition of ascorbate oxidase to the test solution according to Federal Republic of Germany Patent Specification No. 26 25 834.4.

The present invention also provides a reagent for the determination of sulphite, which contains sulphite oxidase, NADH peroxidase, NAD, NADH and a buffer.

This reagent makes possible a simple, specific and quick determination of sulphite.

In a state ready for use, the reagent preferably contains 0.05 to 0.4 mol/liter of buffer with a pH value range of from 7.5 to 8.5, 100 to 500 μmol/liter NADH, 0.5 to 2.0 mMol/liter NAD, 10 to 100 U/liter NADH peroxidase and 25 to 75 U/liter sulphite oxidase or the corresponding amounts in a dry reagent. For ascorbic acid-containing sample solutions, it is also preferable for the reagent to contain 10 to 50 U/liter ascorbate oxidase.

Especially preferably, the reagent contains 0.1 to 0.3 mol of buffer, 125 to 225 μmol NADH, 0.75 to 1.0 mMol NAD, 40 to 80 U NADH peroxidase and 35 to 60 U sulphite oxidase, referred to 1 liter of solution ready for use.

The process and reagent according to the present invention for the determination of sulphite is characterised by its specificity with regard to sulphite, by a simple carrying out of the determination and by a small expenditure of time. Thus, it is possible to determine sulphite quickly and quantitatively, without other reducing substances being able to falsify the results. The process and reagent according to the present invention is especially suitable for routine analyses. It can be used not only for the determination of sulphite in foodstuffs but also in waste water and in the air. It can also be bound to carrier substances and can be used, for example, in the form of test strips.

The following Examples are given for the purpose of illustrating the present invention:

EXAMPLE 1

Sulphite was determined in various foodstuffs. For this purpose, the following components were successively pipetted into a glass cuvette with 1 cm. layer thickness:

component 1: 2 mg. NAD and 0.4 mg. NADH, dissolved in 1 ml. triethanolamine buffer of pH 8.0;

component 2: 0.01 ml. of enzyme suspension containing 0.1 U NADH peroxidase, 1.9 ml. double distilled water and 0.1 ml. of sample solution.

Into a second cuvette there were pipetted components 1 and 2 and the double distilled water in the same amounts as into the first cuvette and additionally 0.1 ml. of double distilled water instead of the sample solution. The reaction solutions were mixed in both cuvettes and after about 5 minutes the extinctions of the solutions were measured. This gave extinction values $E_1$. After the measurement, the reaction was started by the addition of component 3: 0.05 ml. of enzyme suspension containing 0.13 U sulphite oxidase to each cuvette. They were mixed again and, after cessation of the reaction, which took place after about 15 to 20 minutes, the extinctions of the two solutions were again measured. This gave extinction values $E_2$. The concentration of sulphite in the sample can then be calculated according to the following general equation:

$$c = \frac{V \times MW}{\epsilon \times d \times v \times 1000} \times \Delta E [g./l.]$$

wherein V is the test volume (ml.), v is the sample volume (ml.), MW is the molecular weight of the substance to be determined, d is the layer thickness (cm.), $\epsilon$ is the extinction coefficient of NADH and $\Delta E = (E_1 - E_2)_{sample} - (E_1 - E_2)_{blank}$.

The measurement can be carried out at different wavelengths. For the measurement at 340 nm, there is given the following equation for sulphite:

$$c = 1.960 \times \frac{\Delta E}{6.3} [g. SO_2/l. \text{ sample solution}]$$

If a dilution has been carried out in the preparation of the sample, then this must, of course, be taken into account in calculating the result.

EXAMPLE 2

The total $SO_2$ content of white wine was determined. For this purpose, 0.1 ml. of the white wine to be investigated was used directly in the test as the sample volume. The investigation was carried out in the manner described in Example 1.

EXAMPLE 3

A sulphite determination was carried out in red wine. For this purpose, 25 ml. of red wine were adjusted with aqueous sodium hydroxide solution (2 mol/liter) to a pH of 7.5 to 8.0. The solution was diluted with double distilled water to 50 ml. and left to stand for 10 minutes at ambient temperature. 0.1 ml. of this solution was used as the sample volume for the test. The determination was carried out in the manner described in Example 1.

EXAMPLE 4

A sulphite determination was carried out on fruit juice. In order to remove the ascorbic acid from the juice, 2.0 ml. of the fruit juice were adjusted with aqueous sodium hydroxide solution (2 mol/liter) to pH 5 to 6, mixed with about 20 U ascorbate oxidase solution and left to stand for 10 minutes. Thereafter, the sample was adjusted to pH 7.5 to 8.0 with aqueous sodium hydroxide solution. The solution was diluted with double distilled water to 4.0 ml. and 0.2 ml. of this diluted solution was used in the test as sample solution. The test was carried out in the manner described in Example 1.

EXAMPLE 5

Sulphite was determined in jam. For this purpose, about 100 g. of jam were homogenised in a homogeniser for 30 seconds. 5 g. of this homogenised sample were weighed into a 50 ml. graduated flask and filled with 40 ml. water. The graduated flask was closed and heated to 60° C. for 5 minutes. After cooling to ambient temperature, it was made up to the mark with double distilled water, mixed and filtered. 0.2 ml. of the clear solution were used in the test as the sample volume. The determination was carried out in the manner described in Example 1.

EXAMPLE 6

Sulphite was determined in a potato product. For this purpose, about 5 g. of comminuted and ground potato chips were weighed into a 50 ml. graduated flask. It was filled with 40 ml. double distilled water. The graduated flask was closed and heated to about 60° C. for 5 minutes. After cooling to ambient temperature, it was made up to the mark with double distilled water, mixed and centrifuged. 0.5 ml. of the clear solution was used in the test as the sample volume. The determination took place in the manner described in Example 1.

EXAMPLE 7

Sulphite was determined in a spice sample. For this purpose, the spice was comminuted and mixed. About 100 mg. of the comminuted and ground sample were weighed into a 50 ml. graduated flask and 20 ml. double distilled water added thereto. The graduated flask was closed and kept at about 60° C. for 5 minutes. After cooling to ambient temperature, it was filled up to the mark with double distilled water, mixed and filtered. 0.1 ml. of the clear solution was used as the sample volume for the test. The test was carried out in the manner described in Example 1.

We claim:

1. Process for the enzymatic determination of sulphite, comprising the steps of
   oxidizing the sulphite in a buffered solution with sulphite oxidase to give sulphate and hydrogen peroxide;
   reducing the hydrogen peroxide thereby formed in the presence of NAD and NADH with the enyzme NADH peroxidase; and
   determining the consumption of NADH optically, as a measure of the sulphite.

2. Process according to claim 1, wherein the buffer solution used has a pH value of from 7.5 to 8.5.

3. Process according to claim 2, wherein the buffer solution used has a pH value of from 7.8 to 8.2.

4. Process according to claim 2, wherein triethanolamine buffer is used.

5. Process according to claim 4, wherein the buffer is used in a concentration of from 0.05 to 0.4 mol/liter.

6. Process according to claim 5, wherein the buffer is used in a concentration of from 0.1 to 0.3 mol/liter.

7. Process according to claim 1, wherein NADH is used in a concentration of from 100 to 500 μmol/liter.

8. Process according to claim 7, wherein NADH is used in a concentration of from 125 to 225 μmol/liter.

9. Process according to claim 1, wherein 0.5 to 2.0 mMol/liter NAD is used.

10. Process according to claim 9, wherein 0.75 to 1.00 mMol/NAD is used.

11. Process according to claim 1, wherein 10 to 100 U/liter NADH peroxidase is used.

12. Process according to claim 11, wherein 40 to 80 U/liter NADH peroxidase is used.

13. Process according to claim 1, wherein 25 to 75 U/liter sulphite oxidase is used.

14. Process according to claim 13, wherein 35 to 60 U/liter sulphite oxidase is used.

15. Process according to claim 1, wherein ascorbic acid is removed from the sample solution before carrying out the sulphite determination.

16. Process according to claim 15, wherein ascorbate oxidase is used for removing the ascorbic acid.

17. Process according to claim 1 wherein
    the buffer solution has a pH value of from 7.5 to 8.5;
    NADH is used in a concentration of from 100 to 500 μmole/liter;
    NAD is used in a concentration of from 0.5 to 2.0 mMol/liter;
    NADH peroxidase is used in a concentration of from 10 to 100 U/liter; and
    sulfite oxidase is used in a concentration of from 25 to 75 U/liter.

18. Process according to claim 17 wherein said buffer is tris or triethanolamine buffer, glycylglycine buffer or imidizole buffer used in a concentration of 0.05 to 0.4 moles/liter.

19. Reagent for the enzymatic determination of sulphite, containing sulphite oxidase, NADH, NAD, NADH peroxidase and buffer.

20. Reagent according to claim 19, wherein, in each 1 liter of reagent solution ready for use, there is 0.05 to 0.4 mol of buffer, 100 to 500 μmol NADH, 0.5 to 2.0 mMol NAD, 10 to 100 U NADH peroxidase and 25 to 75 U sulphite oxidase.

21. Reagent according to claim 19 wherein said buffer is triethanolamine buffer.

22. Reagent according to claim 19 wherein, in each 1 liter of reagent solution ready for use, there is 0.1 to 0.3 mol of buffer, 125 to 225 μmol/liter NADH, 0.75 to 1.0 mMol NAD, 40 to 80 U NADH peroxidase and 35 to 60 U sulphite oxidase.

23. Reagent according to claim 19 further containing ascorbate oxidase.

* * * * *